(12) United States Patent
Tabb

(10) Patent No.: US 8,460,717 B2
(45) Date of Patent: Jun. 11, 2013

(54) LIQUID ORAL CARE PRODUCT GEARED TO DISINFECT AND STERILIZE A TOOTHBRUSH HEAD IN A COLLAPSIBLE CONDIMENT LIKE PACKAGE

(76) Inventor: Larry Tabb, Atlanta, GA (US)

( * ) Notice: Subject to any disclaimer, the term of this patent is extended or adjusted under 35 U.S.C. 154(b) by 9 days.

(21) Appl. No.: 12/931,136

(22) Filed: Mar. 14, 2011

(65) Prior Publication Data

US 2011/0183003 A1     Jul. 28, 2011

Related U.S. Application Data

(60) Provisional application No. 61/336,726, filed on Jan. 27, 2010.

(51) Int. Cl.
| *A01N 59/00* | (2006.01) |
| *A01N 31/08* | (2006.01) |
| *A01P 1/00* | (2006.01) |
| *B65D 85/84* | (2006.01) |

(52) U.S. Cl.
USPC ................ 424/661; 424/405; 206/524.1

(58) Field of Classification Search
USPC ...................................... 424/54, 49
See application file for complete search history.

(56) References Cited

U.S. PATENT DOCUMENTS

| 3,639,571 | A  | * | 2/1972 | Turesky et al. | ........ 424/54 |
| 6,899,865 | B2 | * | 5/2005 | Eshita | ........ 424/49 |
| 7,306,788 | B2 | * | 12/2007 | McGill et al. | ........ 424/49 |
| 7,592,025 | B2 | * | 9/2009 | Dodds et al. | ........ 424/775 |
| 2005/0210615 | A1 | * | 9/2005 | Shastry et al. | ........ 15/210.1 |

* cited by examiner

*Primary Examiner* — Walter Webb

(57) ABSTRACT

The invention relates to an oral care liquid composition in a unique collapsible, air-tight, condiment like package geared toward sterilize and disinfect a toothbrush head.

The product is poured onto a toothbrush head removing potentially harmful bacteria and germs from their toothbrush head.

1 Claim, 6 Drawing Sheets

LIQUID ORAL CARE PRODUCT GEARED TO DISINFECT AND STERILIZE A TOOTHBRUSH HEAD IN A COLLAPSIBLE CONDIMENT LIKE PACKAGE

BACKGROUND

The increasing link between oral health and overall health is focusing much more attention on the need for preventative oral healthcare. As a result, there is a growing demand for more and better preventative care solution.

Toothbrush sanitizers have become available at a time when people are more conscious about the transferring of germs and the way in which certain cleaners can help people avoid spreading illness. Hand sanitizers, purifiers, cleaning wipes and antibacterial soaps are some of the most common household cleaners sold today. The one thing that is not being sanitized before entering the mouth was a toothbrush.

The (germ) preventive, antibacterial and sanitizer market is one of the largest and fastest growth categories in the supermarket today. With the introduction of many new products and significant increases in marketing spending, this category has experienced significant growth in sales and household penetration.

Protect your family's health: toothbrushes can harbor dangerous bacteria and virus which invite re-infection and the spread of illnesses from other family members. This new product would prevent the transfer of germs and bacteria caused by toothbrushes.

Heart disease and stroke have been linked to oral bacteria. Research done on arteries of stroke victims indicate 40% of bacteria contained in them come from the mouth. This product kills the bacteria that live on your toothbrush to keep your mouth healthy.

There are many ways in which bacteria latch on to a toothbrush: Use from an infected user, spray from a flushing toilet, a damp environment that allows the bacteria to breed and grow. People are clearly becoming more hygiene conscious in the wake of the flu pandemic and more aware that the best way to prevent the flu from spreading.

Most people only give their toothbrush a good rinse when they are done brushing and then place the toothbrush in a warm and dark environment that is ideal for the growth of bacteria and even pathogens.

Today's consumers are more conscious about the transferring of germs and how certain cleaners can help people avoid spreading illness.

Consumer and dental professionals report that on-the-go (OTG) oral care in the workplace is a very important market to target over the next ten years.

While this product would be new to the market, initial reaction among dental professional, consumers and the communities has been favorable. Given the maturity of the oral care segment and the weak economy, these oral care products that offer added benefits and convenience are predicted to be key growth drivers.

There is no doubt that this product will enhance the quality of life making consumer's lives easier.

BACKGROUND AND SUMMARY OF THE INVENTION

This summary is provided to introduce a section of concepts in a simplified form that are further described below in the detailed description of illustrative embodiment. This summary is not intended to be used to limit the scope of the invention.

The invention is a chemical disinfectant and sterilant composition that is packaged in a unique collapsible, air-tight condiment like package, geared toward consumers who are looking for a more convenient, faster way to sterilize and disinfect their toothbrush head. The disinfectant and sterilizer is specifically intended as a means of fighting organisms that cause disease. The disinfectant and sterilizer is intended to eliminate bacteria and germs that are found on a toothbrush head. The liquid product contains chlorine dioxide and flavoring or thymol and flavoring. Chlorine dioxide and Thymol is associated with antibacterial properties; thus, molecular chlorine dioxide or thymol will inhibit growth of bacteria in the mouth and on a toothbrush. Chlorine dioxide and Thymol or used in mouthwash, rinses and other oral care compositions. Our studies with dental professionals have proven that this product effectively eliminates 99% of germs caused by yeast, molds, viruses and bacteria that would otherwise live and multiply on a toothbrush head. This product can protect families from the introduction of illness-causing microorganisms, re-infection, and cross-contamination.

Figure 1:
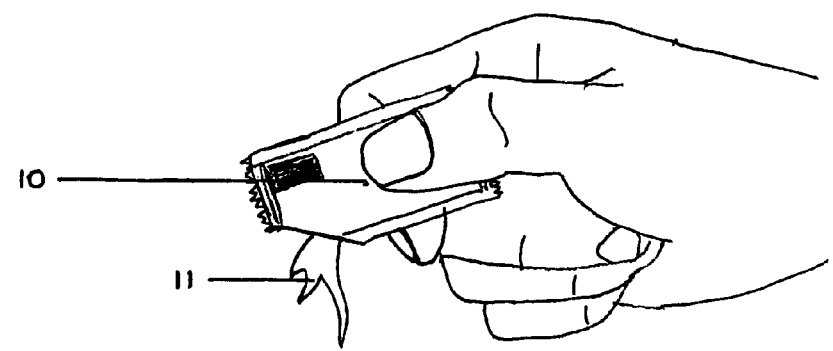
FIG. 1 is an illustration of the fluid container in use after an edge is torn off to open the package through which the fluid is expelled.
Figure 1:
Figure 2:
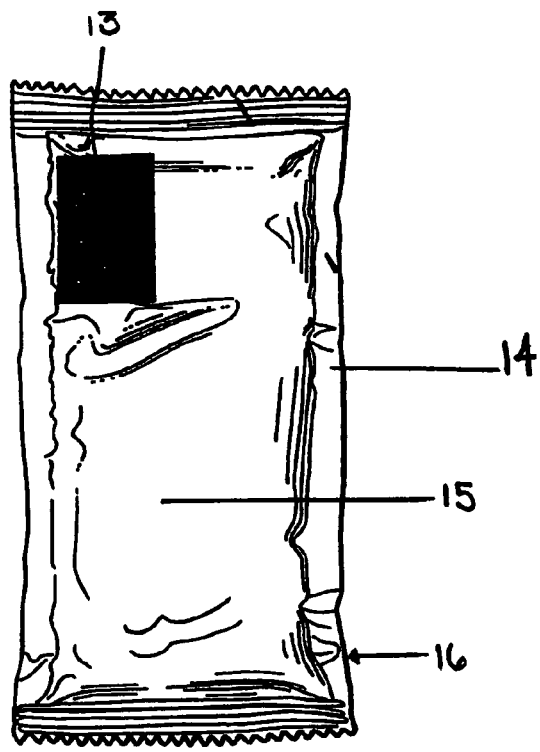
FIG. 2 is a front view of a condiment packet.
Figure 3:
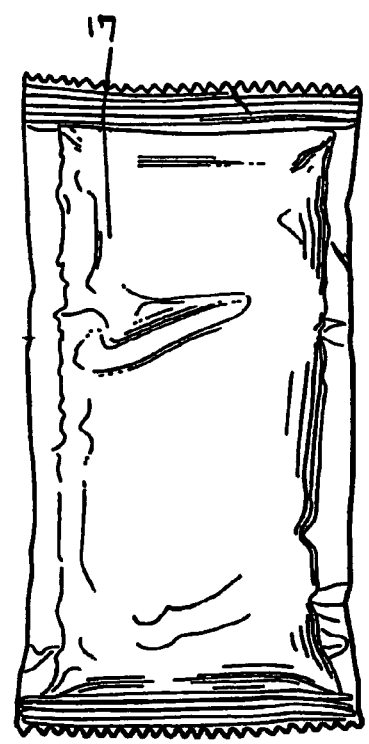
FIG. 3 is a back view of a condiment packet.
Figure 4:
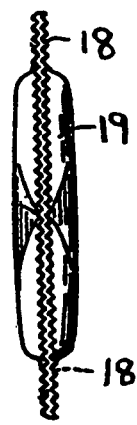
FIG. 4 is a top-sectional view of the filled liquid item.
Figure 5:
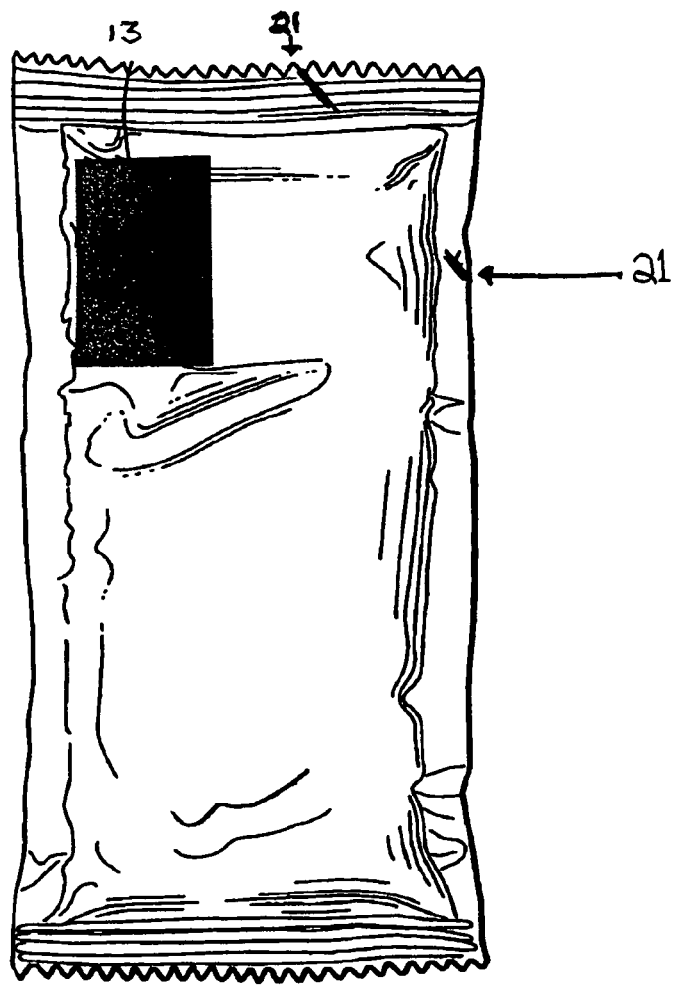
FIG. 5 condiment like packet with a top and side tear line.
Figure 6:
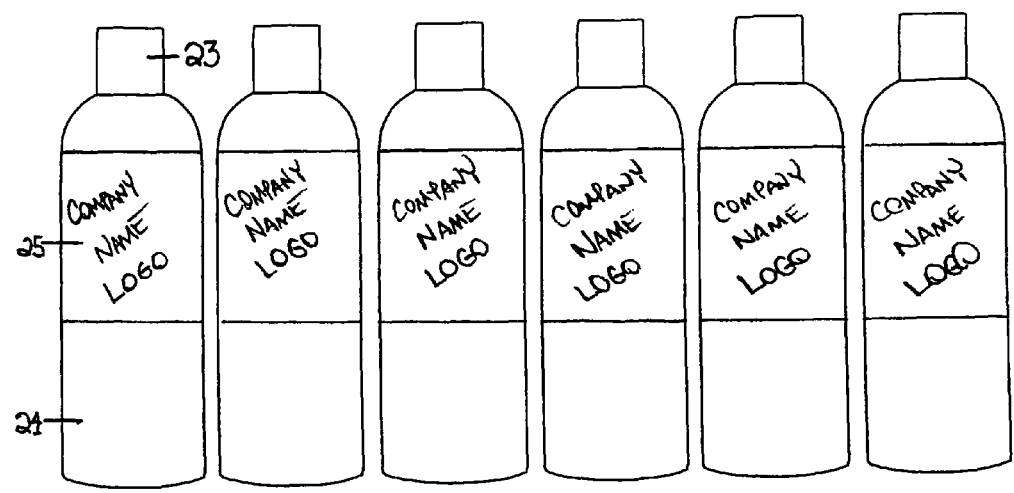
FIG. 6 plastic bottle equipped with a cap suitable for squeezing or pouring and is able to stand right side up and upside down.

The product is poured onto a toothbrush head that can remove potential harmful bacteria and germs from the toothbrush head See FIG. 1. The product is packaged in two ways. It is available in a collapsible, air-tight condiment like (e.g. ketchup) package See FIG. 2, 3, 4. The package is a square, flexible pouch See FIG. 4. Once the condiment packet 16 is opened, the contents 11 may be dispensed onto the toothbrush head 12 by holding the condiment packet by the gripping surface. The flexible square pouches are made of any material suitable for containing chemical liquid, such as thermoplastic films, foil—plastic laminates, or paper—plastic laminates. The package is fabricated from two rectangular pieces of plastic film that are sealed together 14, 18 along the edges so that the chemical is hermetically sealed within the packet. The sealed packet protects the chemical from exposure to ambient air until the user opens the packet. The packet is intended for single uses 16. As shown in FIGS. 2 and 3, the body 16 of the condiment packet further includes frangible bubble 17. See FIG. 5 To open the packet and use the product, the user must tear a small portion of the packet along the cut zone 21 and squeeze 10 or pour the product onto the toothbrush. See FIG. 6. The product is also packaged in an upright, squeezable, capped container See FIG. 6. The packet comprise of plastic 24 wherein the bottle is equipped with a cap 23 suitable for squeeze or pouring and is able to stand right side up and upside down. The bottles are also shaped so that they will nestle against one another with very little clearance. When the bottle is ready to be used for dispensing chemical, the cap is removed and the bottle is turned upside down which then the content may escape though the dispensing nozzle.

Labeling, brand name and logo 13, 22 is also another means for enhancing the marketing appeal of the package.

Figure 7:
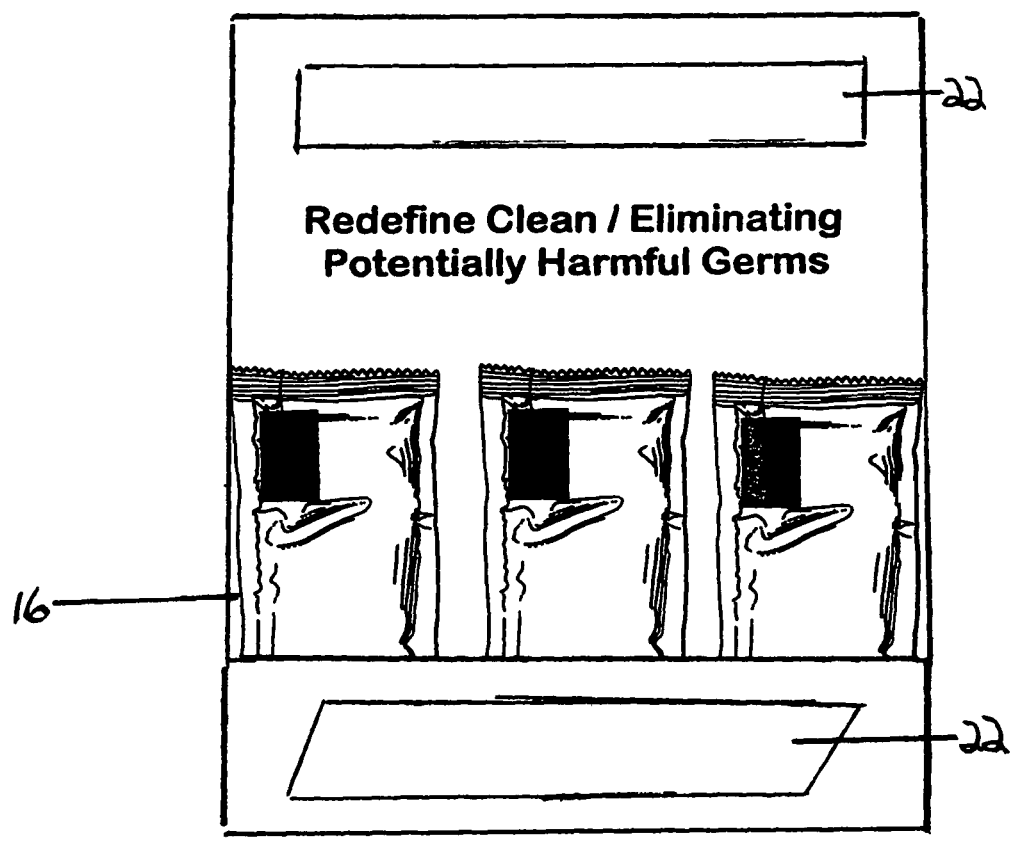
FIG. 7 merchandized as a individual travel-size packaging. A Counter Display for Single Packet Sales, pack hold over 12 units.

See FIG. 7 a condiment package is pack into a display type package for point of sales. The individual packages are place together in a free standing upright poison.

Figure 8:
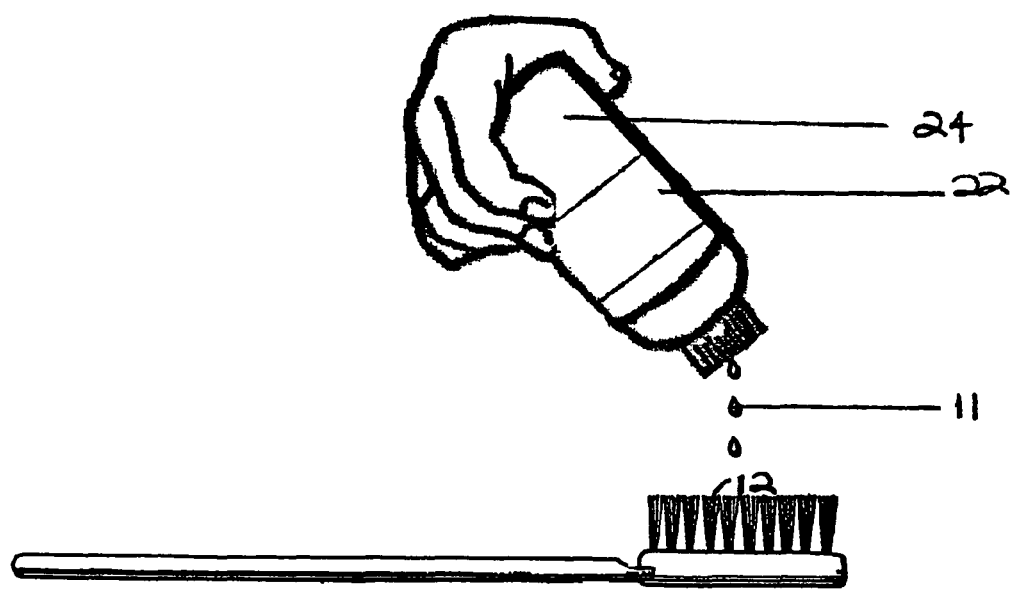
FIG. 8 plastic bottle equipped with a cap suitable for squeezing or pouring.

See FIG. 8 Plastic bottle equipped with a cap 23 suitable for squeeze or pouring and is able to stand right side up and upside down.

This product can protect families from the introduction of illness-causing microorganisms, re-infection, and cross-contamination.

ADVANTAGES COMPARED TO ULTRAVIOLET AND OTHER PRODUCTS

1. Unique collapsible air tight condiment like package geared toward sterilizing and disinfecting a toothbrush head.
2. Maintenance free: no expensive ultraviolet light or bulbs to replace.
3. Work well with all types of brushes, whether it is rotary, or manual, it can be sanitized.
4. Space: do not take up valuable countertop space.
5. Great taste and smell.

SUMMARY OF INVENTION

The invention relates to an oral care liquid composition in a unique collapsible, air-tight, condiment like package intended to sterilize and disinfect a toothbrush head. See FIG. 2 and FIG. 6 the name of the product is call Tabb Brush and Germ Protector, the product is geared toward consumers who are looking for a convenient, faster way to sterilize their toothbrush. The liquid product contains chlorine dioxide and flavoring or thymol and flavoring 11. It comes in a variety of flavors including a flavor-free version. The product is poured onto a toothbrush head See FIG. 1 and FIG. 8, removing potentially harmful bacteria and germs from the toothbrush head. This invention can be used on ether rotary or manual. This product has the potential to make a positive difference in the lives of people by preventing serious diseases worldwide.

The invention claimed is:

1. A chemical composition, comprising a thymol compound, flavoring, and chlorine dioxide packaged in a collapsible, air-tight, condiment-like package, wherein said chemical composition is capable of being poured onto a toothbrush head, whereby the toothbrush head is sterilized and disinfected.

* * * * *